(12) United States Patent
Hong et al.

(10) Patent No.: US 9,096,418 B2
(45) Date of Patent: Aug. 4, 2015

(54) ULTRASONIC TRANSDUCER AND METHOD OF MANUFACTURING THE SAME

(71) Applicant: Samsung Electronics Co., Ltd., Suwon-si (KR)

(72) Inventors: Seog-woo Hong, Yongin-si (KR); Dong-kyun Kim, Suwon-si (KR); Byung-gil Jeong, Anyang-si (KR); Seok-whan Chung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 13 days.

(21) Appl. No.: 14/012,350

(22) Filed: Aug. 28, 2013

(65) Prior Publication Data

US 2014/0061826 A1    Mar. 6, 2014

(30) Foreign Application Priority Data

Aug. 29, 2012  (KR) .................. 10-2012-0095002

(51) Int. Cl.
| | |
|---|---|
| *H01L 29/84* | (2006.01) |
| *B81B 3/00* | (2006.01) |
| *B81C 1/00* | (2006.01) |
| *A61B 8/00* | (2006.01) |

(52) U.S. Cl.
CPC ............. *B81B 3/0027* (2013.01); *A61B 8/4483* (2013.01); *B81C 1/00158* (2013.01)

(58) Field of Classification Search
CPC ...... H01L 27/12; H01L 27/1214; H01L 29/84

USPC ............................................ 257/40, E29.024
See application file for complete search history.

(56) References Cited

U.S. PATENT DOCUMENTS

| | | | |
|---|---|---|---|
| 7,545,075 B2 | 6/2009 | Huang et al. | |
| 7,545,668 B2 * | 6/2009 | Philipp et al. ................. | 365/148 |
| 7,741,686 B2 | 6/2010 | Khuri-Yakub et al. | |
| 7,843,022 B2 | 11/2010 | Kupnik et al. | |
| 7,846,102 B2 | 12/2010 | Kupnik et al. | |
| 2002/0020554 A1 * | 2/2002 | Sakamoto et al. ............ | 174/261 |
| 2007/0299345 A1 * | 12/2007 | Adachi et al. ................. | 600/459 |
| 2008/0023830 A1 * | 1/2008 | Chang et al. ................. | 257/737 |
| 2008/0048211 A1 * | 2/2008 | Khuri-Yakub et al. ....... | 257/204 |
| 2010/0201222 A1 * | 8/2010 | Adachi et al. ................. | 310/317 |
| 2011/0121413 A1 * | 5/2011 | Allen et al. ................... | 257/416 |
| 2011/0140212 A1 | 6/2011 | Itoh et al. | |

FOREIGN PATENT DOCUMENTS

KR    10-2013-0021657 A    3/2013

* cited by examiner

*Primary Examiner* — Thao X Le
*Assistant Examiner* — Patricia Reddington
(74) *Attorney, Agent, or Firm* — Sughrue Mion, PLLC

(57) ABSTRACT

An ultrasonic transducer and a method of manufacturing the same are disclosed. The ultrasonic transducer includes a first electrode layer which is disposed to cover a conductive substrate and an inner wall and a top of a via hole penetrating a membrane and has a top surface at a same height as a top surface of the membrane; a second electrode layer which is disposed on a bottom surface of the conductive substrate to be spaced apart from the first electrode layer; and a top electrode which is disposed on the top surface of the membrane and which contacts the top surface of the first electrode layer.

14 Claims, 7 Drawing Sheets

ULTRASONIC TRANSDUCER AND METHOD OF MANUFACTURING THE SAME

CROSS-REFERENCE TO RELATED APPLICATION

This application claims the benefit of Korean Patent Application No. 10-2012-0095002, filed on Aug. 29, 2012, in the Korean Intellectual Property Office, the disclosure of which is incorporated herein in its entirety by reference.

BACKGROUND

1. Field

The present disclosure relates to ultrasonic transducers and methods of manufacturing the same, and more particularly, to capacitive micromachined ultrasonic transducers (MUTs) and methods of manufacturing the same.

2. Description of the Related Art

A micromachined ultrasonic transducer (MUT) is a device for converting electric signals to ultrasonic signals or vice versa. According to transducing methods, MUTs may be implemented as a variety of different types, such as, for example, a piezoelectric MUT (PMUT), a capacitive MUT (CMUT), a magnetic MUT (MMUT), etc. From among various types of MUTs, a CMUT is popularly used in medical image diagnosing devices or sensors. A CMUT has a structure including a thin membrane and support substrates separated by a cavity. Such a CMUT requires high operational uniformity throughout a large area.

SUMMARY

Provided are capacitive micromachined ultrasonic transducers (CMUTs) and methods of manufacturing the same.

Additional aspects will be set forth in part in the description which follows and, in part, will be apparent from the description, or may be learned by practice of the presented exemplary embodiments.

According to an aspect of an exemplary embodiment, an ultrasonic transducer includes a conductive substrate; a support which is disposed on the conductive substrate and includes cavities; a membrane which is disposed on the support to cover the cavities; a first electrode layer which is disposed to cover the conductive substrate and an inner wall and a top of a via hole penetrating the membrane, the first electrode layer having a top surface at a same height as a top surface of the membrane; a second electrode layer which is disposed on a bottom surface of the conductive substrate to be spaced apart from the first electrode layer; a top electrode which is disposed on the top surface of the membrane and which contacts the top surface of the first electrode layer; and a pad substrate which is disposed below the conductive substrate and has formed thereon bonding pads electrically connected to the first and second electrode layers.

An element separation line may penetrate through the membrane and the top electrode. The inner wall of the via hole and an inner wall of the element separation line contacting the top electrode may have rounded shapes.

The membrane may contain silicon, and the support may contain silicon oxide. Silicon oxide may be formed on an inner wall of the element separation line. An insulation material may be formed on the inner wall of the via hole.

An upper insulation layer and a lower insulation layer may be respectively formed on a top surface and a bottom surface of the conductive substrate. The lower insulation layer may be patterned such that the second electrode layer contacts the bottom surface of the conductive substrate.

The first and second electrode layers may contain at least one of Au and Cu, and the first and second upper pads may contain at least one from among Au, Cu, and Sn.

The plurality of bonding pads may be disposed on a top surface of the pad substrate and may include a first upper pad and a second upper pad that are respectively bonded to the first electrode layer and the second electrode layer. The plurality of bonding pads may further include first and second lower pads, which are disposed on a bottom surface of the pad substrate and are electrically connected to the first and second upper pads. An eutectic alloy may be formed due to eutectic bonding at an interface between the first electrode layer and the first upper pad and an interface between the second electrode layer and the second upper pad.

According to another aspect of an exemplary embodiment, a method of manufacturing an ultrasonic transducer includes preparing a first wafer including a first lower substrate, a first insulation layer, and a first upper substrate that are stacked in order and forming a first via hole and an element separation line by patterning the first upper substrate; forming a support including cavities on the patterned first upper substrate; preparing a second wafer including a second substrate and a second insulation layer formed on a first surface of the second substrate and bonding the second insulation layer onto the support to cover the first via hole, the element separation line, and the cavities; forming a via hole including the first via hole and a second via hole by forming the second via hole, which communicates with the first via hole, in the second substrate and the second insulation layer; forming a first electrode layer on an inner wall of the via hole and the first insulation layer, which is exposed by the via hole, and forming a second electrode layer on a second surface of the second substrate; bonding a pad substrate on which bonding pads are formed to the first and second electrode layers; exposing the first electrode layer and the first upper substrate and exposing the element separation line by removing the first lower substrate and the first insulation layer; and forming a top electrode on an exposed top surface of the first electrode layer and an exposed top surface of the first upper substrate.

The first wafer may include a silicon-on-insulator (SOI) wafer. The support may be formed by forming a third insulation layer on the patterned first upper substrate and patterning the third insulation layer. The third insulation layer may include a silicon oxide formed by thermally oxidizing the first upper substrate.

The second substrate may contain conductive silicon, and the second insulation layer may contain a silicon oxide. The second insulation layer may be bonded onto the support via silicon direct bonding (SDB). The method may further include polishing the second substrate to a predetermined thickness after the second insulation layer is bonded.

The method may further include, after the via hole is formed, forming a fourth insulation layer on the inner wall of the via hole and the second surface of the second substrate; and exposing a bottom surface of the second substrate, on which the second electrode layer is to be formed, by patterning the fourth insulation layer.

The first and second electrode layers may be bonded to the first and second upper pads via eutectic bonding. The top electrode may include two portions which are separated by the element separation line.

BRIEF DESCRIPTION OF THE DRAWINGS

These and/or other aspects will become apparent and more readily appreciated from the following description of the exemplary embodiments, taken in conjunction with the accompanying drawings of which.

DETAILED DESCRIPTION OF THE EXEMPLARY EMBODIMENTS

Figure 1:
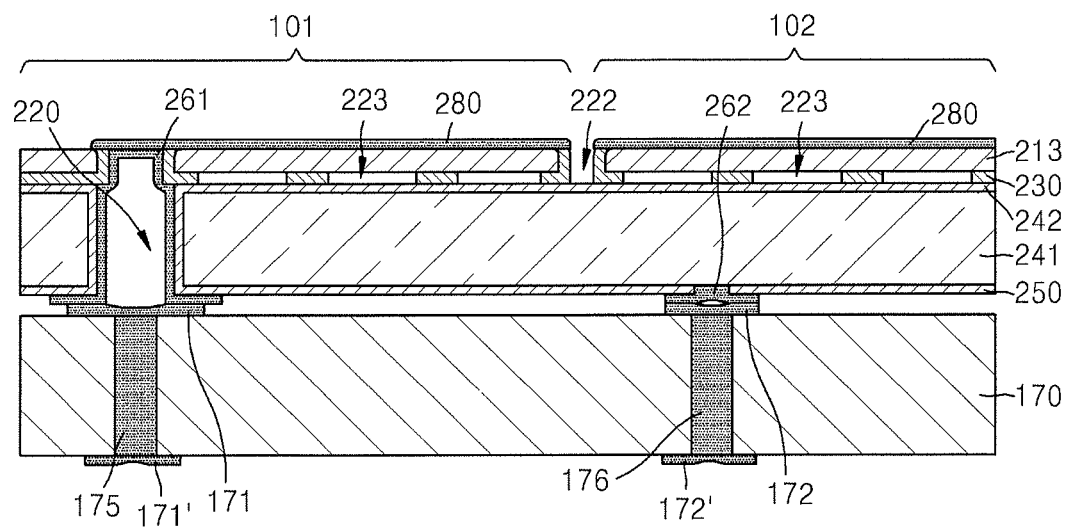
FIG. 1 is a diagram showing a capacitive micromachined ultrasonic transducer (CMUT) according to an exemplary embodiment.

Reference will now be made in detail to exemplary embodiments, examples of which are illustrated in the accompanying drawings, wherein like reference numerals refer to like elements throughout. Accordingly, the exemplary embodiments are merely described below, by referring to the figures, to explain aspects of the present disclosure. Expressions such as "at least one of," when preceding a list of elements, modify the entire list of elements and do not modify the individual elements of the list.

The present disclosure will now be described more fully with reference to the accompanying drawings, in which exemplary embodiments are shown. The exemplary embodiments may, however, be embodied in many different forms and should not be construed as being limited to the exemplary embodiments set forth herein; rather, these exemplary embodiments are provided so that this disclosure will be thorough and complete, and will fully convey the concept of the exemplary embodiments to those of ordinary skill in the art. In the drawings, the thicknesses of layers and regions are exaggerated for clarity. It will also be understood that when a layer is referred to as being "on" another layer or substrate, it can be directly on the other layer or substrate, or intervening layers may also be present. Like reference numerals in the drawings denote like elements, and thus their description will not be repeated. Furthermore, materials constituting layers provided in the exemplary embodiments described below are merely examples, and the layers may be formed of other materials.

FIG. 1 is a diagram showing a capacitive micromachined ultrasonic transducer (CMUT) according to an exemplary embodiment.

Referring to FIG. 1, the CMUT according to the present exemplary embodiment includes a plurality of elements 101 and 102 that are 2-dimensionally arranged, where each of the elements 101 and 102 includes at least one cavity 223. According to exemplary embodiments, the elements 101 and 102 are separated from each other by an element separation line 222 for preventing crosstalk and electric signal connection between the elements 101 and 102.

The CMUT includes a conductive substrate 241, a support 230 and a membrane 213 that are arranged on top of the conductive substrate 241, and a pad substrate 170 arranged below the conductive substrate 241. The conductive substrate 241 may function as a bottom electrode. For example, the conductive substrate 241 may be implemented as a low resistance silicon substrate. However, the exemplary embodiments are not limited thereto. An upper insulation layer 242 may be formed on the top surface of the conductive substrate 241. The upper insulation layer 242 may contain a silicon oxide, for example. However, the exemplary embodiments are not limited thereto.

The support 230, in which a plurality of cavities 223 is formed, is arranged on the upper insulation layer 242. The support 230 may contain silicon oxide. However, the exemplary embodiments are not limited thereto. The membrane 213 is arranged on the support 230 to cover the cavities 223. The membrane 213 may be formed of silicon. However, the exemplary embodiments are not limited thereto. A via hole 220 is formed to penetrate through the conductive substrate 241, the upper insulation layer 242, and the membrane 213. An insulation material, such as a silicon oxide, may be formed on the inner wall of the via hole 220.

A first electrode layer 261 is arranged to cover the inner wall and the top of the via hole 220. Here, the first electrode layer 261 may be formed such that the top surface of the first electrode layer 261 is at the same height as the top surface of the membrane 213. A lower insulation layer 250 may be formed on the bottom surface of the conductive substrate 241. According to exemplary embodiments, the lower insulation layer 250 is patterned to expose a portion of the bottom surface of the conductive substrate 241, and a second electrode layer 262 is formed to contact the exposed portion of the bottom surface of the conductive substrate 241. The first electrode layer 261 and the second electrode layer 262 may contain conductive materials. For example, the first electrode layer 261 and the second electrode layer 262 may contain at least one conductive material selected from among Au and Cu. However, the exemplary embodiments are not limited thereto.

A top electrode 280 is arranged on the top surface of the membrane 213 to contact the first electrode layer 261. The top electrode 280 is arranged on the top surface of the first electrode layer 261 and the top surface of the membrane 213, which are at the same height. As described below, the upper portion of the inner wall of the via hole 220 contacting the top electrode 280 may have a rounded shape by being notched in an etching operation, and thus, an area where the top electrode 280 contacts the first electrode layer 261 may increase. As a result, an electrical connection between the top electrode 280 and the first electrode layer 261 may be established with ease, and thus, disconnection between the first electrode layer 261 and the top electrode 280 may be prevented.

Furthermore, the element separation line 222 separating the elements 101 and 102 from each other may be formed by penetrating the top electrode 280 and the membrane 213. According to exemplary embodiments, an insulation material constituting the support 230, e.g., a silicon oxide, may be formed on the inner wall of the element separation line 222. The upper insulation layer 242 may be exposed by the element separation line 222. As described below, the upper portion of the inner wall of the element separation line 222 contacting the top electrode 280 may have a rounded shape by being notched in an etching operation, and thus, insulation between the elements 101 and 102 may be improved.

The pad substrate 170 is arranged below the conductive substrate 241. The pad substrate 170 may be a silicon substrate, for example. However, the exemplary embodiments are not limited thereto. A plurality of bonding pads that are electrically connected to the first electrode layer 261 and the second electrode layer 262 are formed on the pad substrate 170. The bond pads are arranged on the top surface of the pad substrate 170 and include first and second upper pads 171 and 172 that are bonded to the first electrode layer 261 and the second electrode layer 262, respectively. The first and second upper pads 171 and 172 may contain conductive materials. For example, the first and second upper pads 171 and 172 may contain at least one conductive material selected from among Au, Cu, and Sn. However, the exemplary embodiments are not limited thereto. For example, the first and second upper pads 171 and 172 may include Au/Sn layers.

Bonding between the first electrode layer 261 and the first upper pad 171 and bonding between the second electrode layer 262 and the second upper pad 172 may be implemented through eutectic bonding. For example, if the first electrode layer 261 is formed of an Au layer and the first upper pad 171 is formed of an Au/Sn layer, when the first electrode layer 261 and the first upper pad 171 are eutectically bonded, an Au—Sn eutectic alloy may be formed at the interface between the first electrode layer 261 and the first upper pad 171. Alternatively, the bonding between the first electrode layer 261 and the first upper pad 171 and the bonding between the second electrode layer 262 and the second upper pad 172 is not limited to being implemented by eutectic bonding according to other exemplary embodiments.

First and second lower pads 171' and 172', which are electrically connected to the first upper pad 171 and the second upper pad 172, respectively, may be formed on the bottom surface of the pad substrate 170. A first conductive filling 175 which electrically interconnects the first upper pad 171 and the first lower pad 171' and a second conductive filling 176 which electrically interconnects the second upper pad 172 and the second lower pad 172' are arranged inside the pad substrate 170. Here, the first and second lower pads 171' and 172' may contain the same conductive materials as the first upper pad 171 and the second upper pad 172. However, the exemplary embodiments are not limited thereto.

Hereinafter, a method of manufacturing the CMUT as described above will be described. FIGS. 2, 3A, 3B, 4, 5A, 5B, 6, 7, 8, 9, 10, 11, 12, 13A, and 13B are diagrams for describing methods of manufacturing the CMUT shown in FIG. 1 according to exemplary embodiments.

Figure 2:
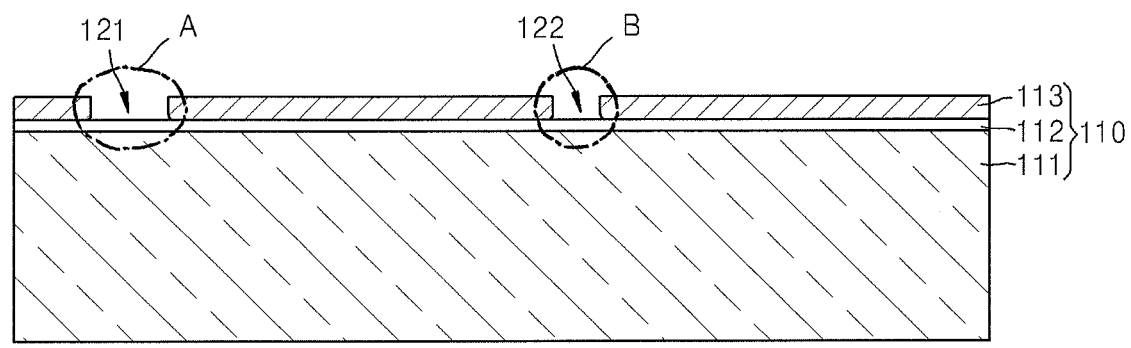
FIGS. 2, 3A, 3B, 4, 5A, 5B, 6, 7, 8, 9, 10, 11, 12, 13A, and 13B are diagrams for describing methods of manufacturing the CMUT shown in FIG. 1 according to exemplary embodiments.
Figure 3A:
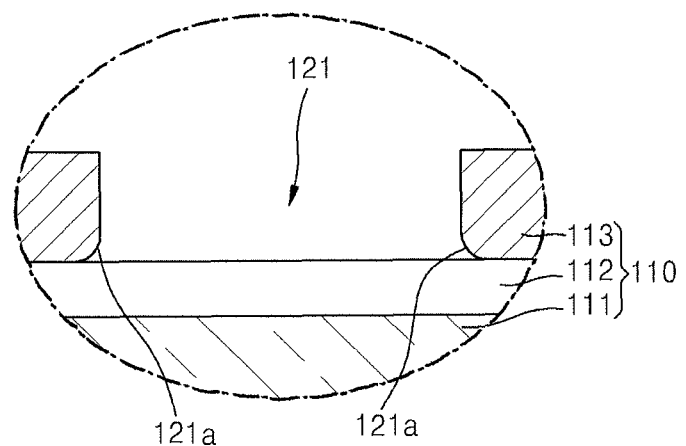
Figure 3B:
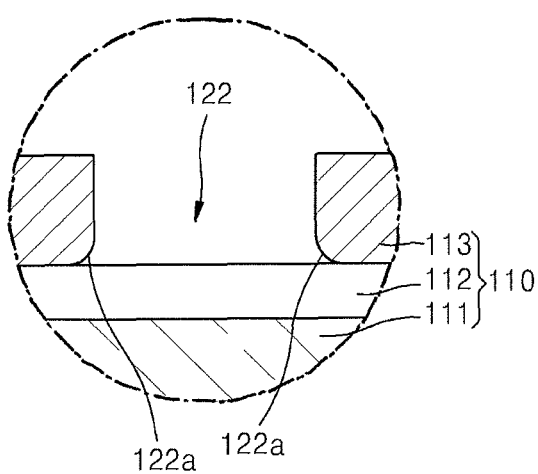

Referring to FIG. 2, a first wafer 110 including a first lower substrate 111, a first insulation layer 112, and a first upper substrate 113 that are stacked in the order stated is provided. The first wafer 110 may be a silicon on insulator (SOI) substrate, for example. According to exemplary embodiments, the first upper substrate 113 forms a membrane, as described below. Next, a first via hole 121 and an element separation line 122 are formed by patterning the first upper substrate 113. FIGS. 3A and 3B are diagrams showing the section A (the first via hole 121) and the section B (the element separation line 122) of FIG. 2 in more detail, respectively. Referring to FIG. 3A, due to an undercut resulting from etching of the first upper substrate 113, a lower inner wall 121a of the first via hole 121 contacting the first insulation layer 112 may have a rounded shape. Furthermore, referring to FIG. 3B, due to a notch resulting from etching of the first upper substrate 113, a lower inner wall 122a of the element separation line 122 contacting the first insulation layer 112 may have a rounded shape.

Figure 4:
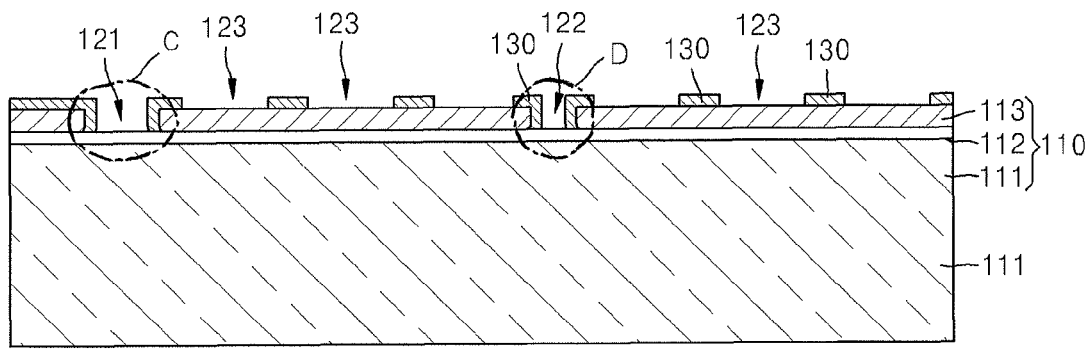
Figure 5A:
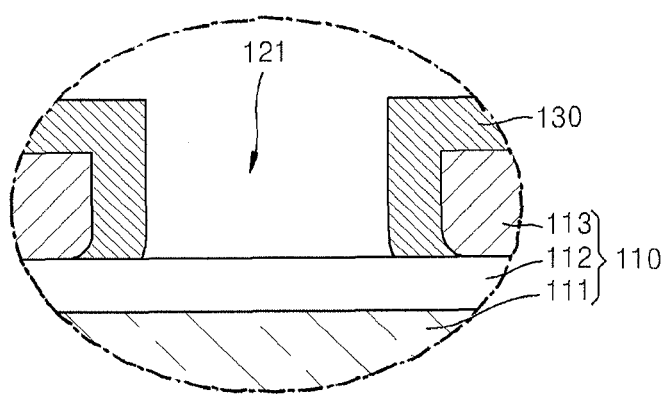
Figure 5B:
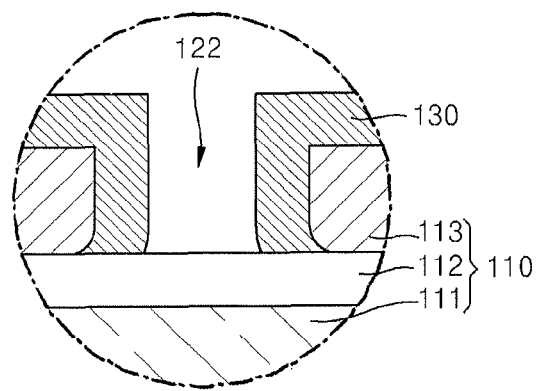

Referring to FIG. 4, a third insulation layer 130 including a plurality of cavities 123 is formed by forming a layer (e.g., a predetermined material layer) on the patterned first upper substrate 113 and patterning the predetermined material layer. The third insulation layer 130 constitutes a support. The third insulation layer 130 may be formed by patterning a silicon oxide layer that is formed by thermally oxidizing the first upper substrate 113 formed of silicon. The third insulation layer 130 may be formed on both the inner wall of the first via hole 121 and the inner wall of the element separation line 122. FIGS. 5A and 5B are diagrams showing the section C (the first via hole 121) and the section D (the element separation line 122) of FIG. 4 in more detail, respectively. Referring to FIG. 5A, the third insulation layer 130 formed on the inner wall of the first via hole 121 may be formed to have a shape corresponding to that of the inner wall of the first via hole 121. Furthermore, referring to FIG. 5B, the third insulation layer 130 formed on the inner wall of the element separation line 122 may be formed to have a shape corresponding to that of the inner wall of the element separation line 122.

Figure 6:
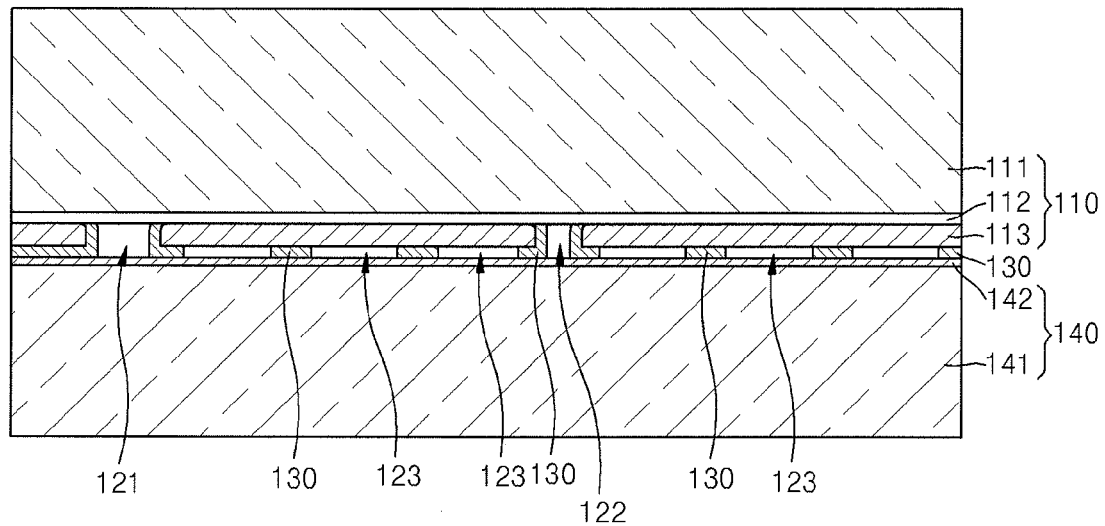
Figure 7:
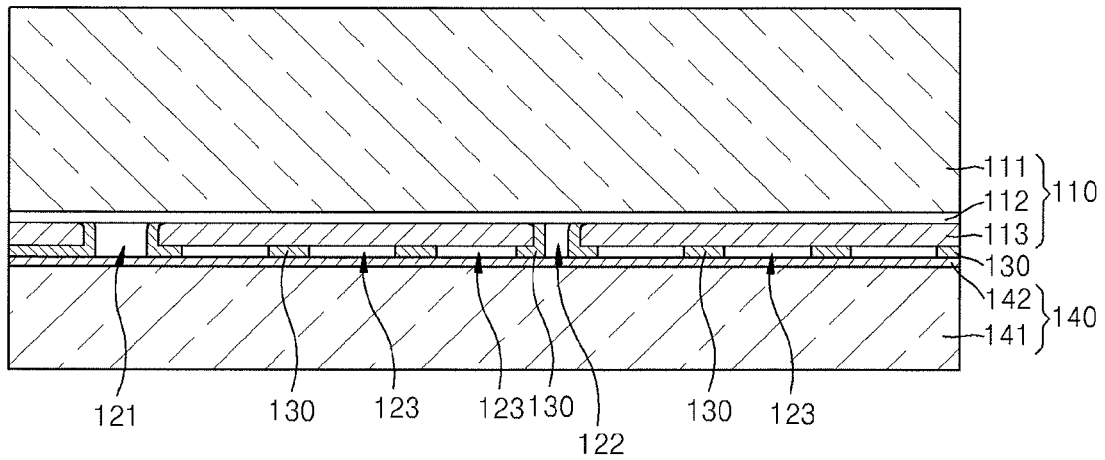

Referring to FIG. 6, a second wafer 140, which includes a second substrate 141 and a second insulation layer 142 formed on the top surface of the second substrate 141, is provided. According to exemplary embodiments, the second substrate 141 may contain conductive silicon, for example. The second wafer 140 may be implemented as a low resistance wafer including a low resistance silicon substrate and a silicon oxide layer, for example. Next, the second insulation layer 142 of the second wafer 140 is bonded onto the third insulation layer 130 to cover the first via hole 121, the element separation line 122, and the cavities 123. FIG. 6 shows that the structure shown in FIG. 5 is turned upside down and the second wafer 140 is bonded onto the third insulation layer 130. The second insulation layer 142 may be bonded to the third insulation layer 130 via the technique of silicon direct bonding (SDB), for example. Next, referring to FIG. 7, the second substrate 141 may be polished to a desired thickness via chemical mechanical polishing (CMP), for example.

Figure 8:
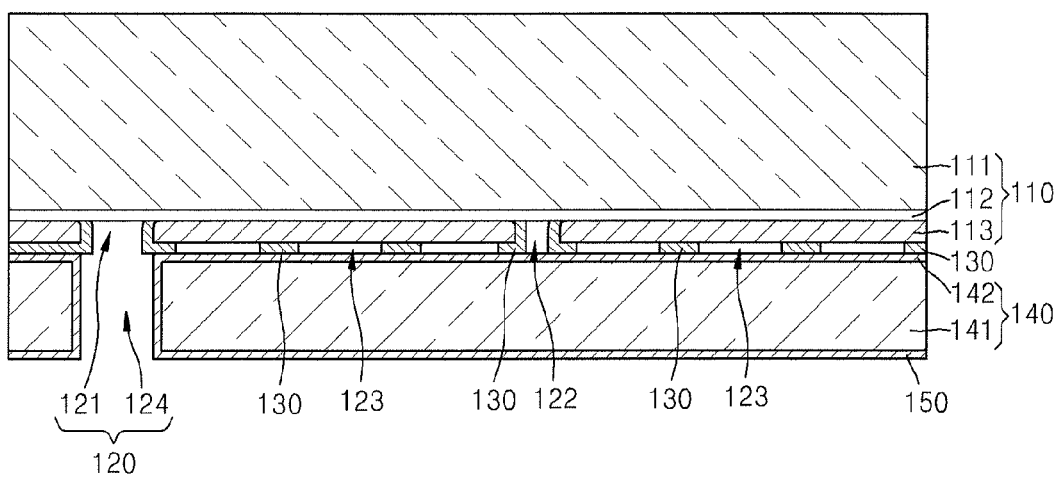

Referring to FIG. 8, a second via hole 124 communicating with the first via hole 121 is formed by etching the second substrate 141 and the second insulation layer 142 that are located below the first via hole 121. Next, a fourth insulation layer 150 is formed on the inner wall of the second via hole 124 and the bottom surface of the second substrate 141. As a result, a via hole 120 including the first and second via holes 121 and 124 communicating with each other is formed.

Figure 9:
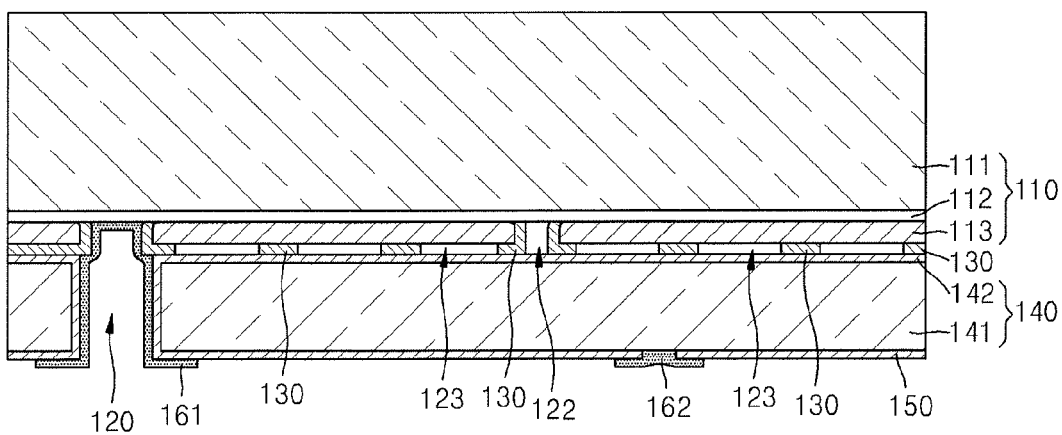

Referring to FIG. 9, the fourth insulation layer 150 formed on the bottom surface of the second substrate 141 is patterned to expose a portion of the bottom surface of the second substrate 141. Next, an electrode material layer is formed on the inner wall of the via hole 120 and the fourth insulation layer 150 formed on the bottom surface of the second substrate 141 and is patterned, thereby forming a first electrode layer 161 and a second electrode layer 162. According to exemplary embodiments, the first electrode layer 161 may be formed on the inner wall of the via hole 120 and on a portion of the first insulation layer 112 covering the top of the via hole 120. Therefore, the top surface of the first electrode layer 161 may be at the same height as the top surface of the first upper substrate 113. Furthermore, the first electrode layer 161 may extend onto the fourth insulation layer 150 formed on the bottom surface of the second substrate 141. The second electrode layer 162 may be formed to contact the portion of the second substrate 141 exposed by the patterned fourth insulation layer 150. The second electrode layer 162 is formed to be spaced apart from the first electrode layer 161. The first electrode layer 161 and the second electrode layer 162 may contain conductive materials. For example, the first electrode layer 161 and the second electrode layer 162 may contain at least one of Au and Cu. However, the exemplary embodiments are not limited thereto.

Figure 10:
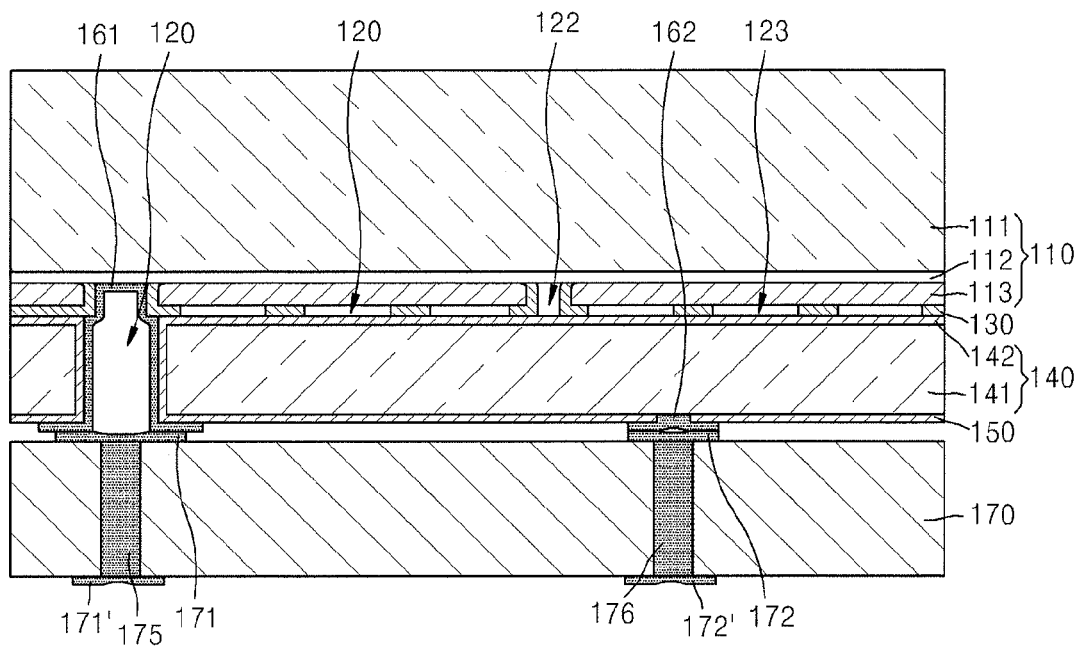

Referring to FIG. 10, a plurality of bonding pads formed on the pad substrate 170 are bonded to the first electrode layer 161 and the second electrode layer 162. The pad substrate 170 may be a silicon substrate, for example. However, the exemplary embodiments are not limited thereto. The bonding pads are arranged on the top surface of the pad substrate 170 and include the first upper pad 171 and the second upper pad 172 that are respectively bonded to the first electrode layer 161 and the second electrode layer 162. According to exemplary embodiments, the first upper pad 171 and the second upper pad 172 may contain conductive materials. For example, the first upper pad 171 and the second upper pad 172 may contain at least one conductive material selected from among Au, Cu, and Sn. However, the exemplary embodiments are not limited thereto. In detail, the first upper pad 171 and the second upper pad 172 may be formed of Au/Sn layers. Bonding between the first electrode layer 161 and the first upper pad 171 and bonding between the second electrode layer 162 and the second upper pad 172 may be implemented using eutectic bonding. For example, if the first electrode layer 161 is formed of an Au layer and the first upper pad 171 is formed of an Au/Sn layer, when the first electrode layer 161 and the first upper pad 171 are eutectically bonded, an Au—Sn eutectic alloy may be formed at the interface between the first electrode layer 161 and the first upper pad 171. Alternatively, the bonding between the first electrode layer 161 and the first upper pad 171 and the bonding between the second electrode layer 162 and the second upper pad 172 is not limited to being implemented using eutectic bonding, and may instead be implemented using other types of bonding known to those skilled in the art.

The first and second lower pads 171' and 172', which are electrically connected to the first upper pad 171 and the second upper pad 172, respectively, may be formed on the bottom surface of the pad substrate 170. The first conductive filling 175 which electrically interconnects the first upper pad 171 and the first lower pad 171' and the second conductive filling 176 which electrically interconnects the second upper pad 172 and the second lower pad 172' are arranged inside the pad substrate 170. According to exemplary embodiments, the first and second lower pads 171' and 172' may contain the same conductive materials as the first upper pad 171 and the second upper pad 172. However, the exemplary embodiments are not limited thereto.

Figure 11:
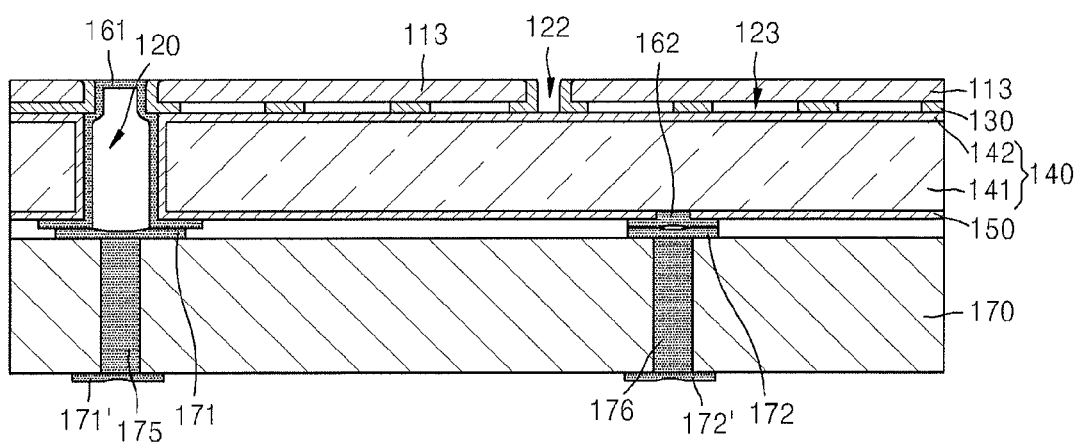
Figure 12:
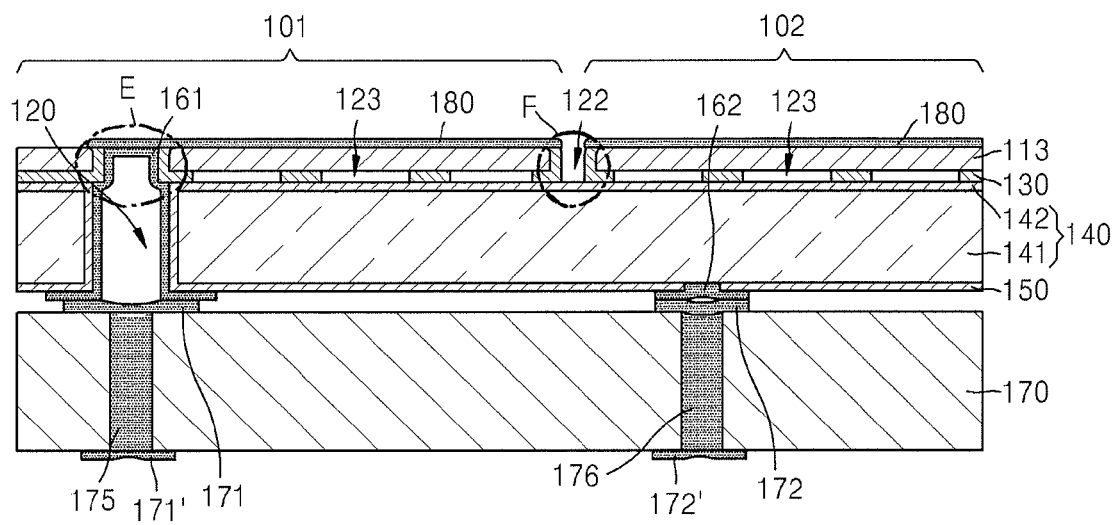
Figure 13A:
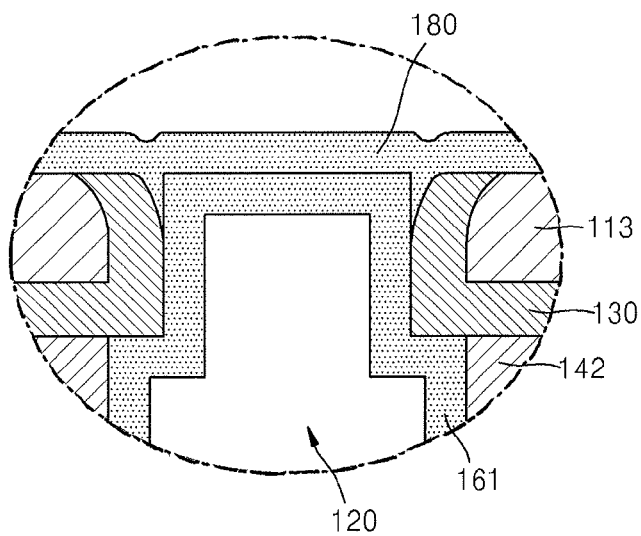
Figure 13B:
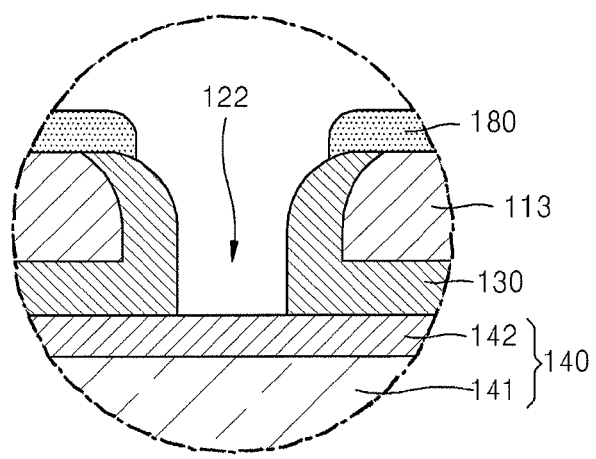

Referring to FIG. 11, the first lower substrate 111 and the first insulation layer 112 are removed. Therefore, the top surface of the first electrode layer 161 and the top surface of the first upper substrate 113 are exposed, and the element separation line 122 is exposed. Referring to FIG. 12, an upper electrode 180 is formed on the top surface of the first upper substrate 113 to contact the first electrode layer 161. The upper electrode 180 may be formed by forming a conductive material on the exposed top surface of the first electrode layer 161 and the exposed top surface of the first upper substrate 113 and patterning the conductive material. According to exemplary embodiments, the upper electrode 180 may be formed into two pieces which are separated by the element separation line 122. FIGS. 13A and 13B are diagrams showing the section E (the via hole 120) and the section F (the element separation line 122) of FIG. 12 in more detail, respectively. Referring to FIG. 13A, due to a notch resulting from etching of the first upper substrate 113 as described above, an upper inner wall of the via hole 120 close to the upper electrode 180 has a rounded shape. Therefore, an area where the upper electrode 180 contacts the first electrode layer 161 increases. Furthermore, referring to FIG. 13B, due to an undercut resulting from etching of the first upper substrate 113, an upper inner wall of the element separation line 122 has a rounded shape. Therefore, the upper electrode 180 formed on the top surface of the first upper substrate 113 may be effectively separated by the element separation line 122, and thus insulation between the elements 101 and 102 may be improved. In the method of manufacturing an ultrasonic transducer according to exemplary embodiments, a via hole, an element separation line, and cavities are formed in a SOI wafer in advance, and a low resistance wafer is bonded thereto, thereby simplifying the overall manufacturing process.

As described above, according to exemplary embodiments, since a top electrode is formed on the top surface of a first electrode layer and the top surface of a membrane that are at a same height and an area where the top electrode contacts the first electrode layer increases, disconnection between the top electrode and the first electrode layer may be prevented. Furthermore, due to an element separation line formed between elements, insulation between the elements may be improved. Furthermore, the overall process for manufacturing an ultrasonic transducer may be simplified by forming cavities, a via hole, and an element separation line in a SOI wafer in advance. It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. An ultrasonic transducer comprising:
   a conductive substrate;
   a support which is disposed on the conductive substrate and includes cavities;
   a membrane which is disposed on the support to cover the cavities;
   a via hole penetrating the conductive substrate and the membrane;
   a first electrode layer which is disposed on an inner wall and a top portion of the via hole, the first electrode layer having a top surface at a same height as a top surface of the membrane;
   a second electrode layer which is disposed on a bottom surface of the conductive substrate to be spaced apart from the first electrode layer;
   a top electrode which is disposed to contact the top surface of the first electrode layer on the top surface of the membrane; and
   a pad substrate which is disposed below the conductive substrate and has formed thereon bonding pads electrically connected to the first and second electrode layers.

2. The ultrasonic transducer of claim 1, wherein an element separation line penetrates through the membrane and the top electrode.

3. The ultrasonic transducer of claim 2, wherein the inner wall of the via hole and an inner wall of the element separation line contacting the top electrode have rounded shapes.

4. The ultrasonic transducer of claim 2, wherein:
   the membrane comprises silicon; and
   the support comprises silicon oxide.

5. The ultrasonic transducer of claim 4, wherein the silicon oxide is formed on an inner wall of the element separation line.

6. The ultrasonic transducer of claim 1, wherein an insulation material is formed on the inner wall of the via hole.

7. The ultrasonic transducer of claim 1, wherein an upper insulation layer and a lower insulation layer are respectively formed on a top surface and a bottom surface of the conductive substrate.

8. The ultrasonic transducer of claim 7, wherein the lower insulation layer is patterned such that the second electrode layer contacts the bottom surface of the conductive substrate.

9. The ultrasonic transducer of claim 1, wherein the bonding pads are disposed on a top surface of the pad substrate and comprise a first upper pad and a second upper pad that are respectively bonded to the first electrode layer and the second electrode layer.

10. The ultrasonic transducer of claim 9, wherein:
    the first and second electrode layers comprise at least one of Au and Cu; and the first and second upper pads comprise at least one from among Au, Cu, and Sn.

11. The ultrasonic transducer of claim 9, wherein the bonding pads further comprise first and second lower pads which are disposed on a bottom surface of the pad substrate and are electrically connected to the first and second upper pads.

12. The ultrasonic transducer of claim 9, wherein an eutectic alloy is formed due to eutectic bonding at an interface between the first electrode layer and the first upper pad and an interface between the second electrode layer and the second upper pad.

13. An ultrasonic transducer comprising:
a conductive substrate;
a membrane formed on the conductive substrate;
a via hole formed in the conductive substrate and the membrane, the via hole defining an internal surface area and an opening;
an electrode layer comprising a first portion covering the internal surface area and a second portion covering the opening; and
an electrode disposed on the second portion,
wherein the electrode layer has a top surface at a same height as a top surface of the membrane,
wherein the via hole is formed such that the internal surface area is curved away from the electrode layer at a boundary of the first and second portions to form a notch into which the electrode is formed, to thereby increase a surface area at which the electrode contacts the electrode layer.

14. The ultrasonic transducer according to claim 13, wherein the ultrasonic transducer comprises a capacitive micromachined ultrasonic transducer (CMUT).

* * * * *